United States Patent [19]

Nashed et al.

[11] Patent Number: 5,567,683

[45] Date of Patent: *Oct. 22, 1996

[54] SUBSTITUTED LACTOSE AND LACTOSAMINE DERIVATIVES AS CELL ADHESION INHIBITORS

[75] Inventors: Mina A. Nashed, Alexandria, Egypt; Falguni Dasgupta, Alameda, Calif.; Saeed A. Abbas, Vallejo, Calif.; John H. Musser, San Carlos, Calif.; Darwin S. Asa, Galesburg, Mich.

[73] Assignee: Glycomed Incorporated, Alameda, Calif.

[ * ] Notice: The term of this patent shall not extend beyond the expiration date of Pat. No. 5,326,752.

[21] Appl. No.: 270,874

[22] Filed: Jul. 1, 1994

Related U.S. Application Data

[63] Continuation of Ser. No. 800,557, Nov. 27, 1991, Pat. No. 5,326,752.

[51] Int. Cl.$^6$ .................. A61K 31/70; A61K 31/715; A61K 37/00; A61K 37/10
[52] U.S. Cl. .................. 514/25; 514/53; 514/2; 514/8; 536/4.1; 536/18.2; 536/18.7; 536/55; 536/55.3
[58] Field of Search .................. 514/25, 53, 2, 514/8; 536/4.1, 18.2, 18.7, 55, 55.3

[56] References Cited

U.S. PATENT DOCUMENTS

| | | | |
|---|---|---|---|
| 4,661,345 | 4/1987 | Tuomanen | 514/8 |
| 4,994,441 | 2/1991 | Neeser | 514/8 |

FOREIGN PATENT DOCUMENTS

| | | | |
|---|---|---|---|
| 579196A1 | 7/1993 | European Pat. Off. | C07H 15/18 |
| WO9202527 | 2/1992 | WIPO | C07H 5/00 |
| WO9207572 | 5/1992 | WIPO | A61K 31/73 |
| WO9218610 | 10/1992 | WIPO | |

OTHER PUBLICATIONS

EPO Supplementary Search Report for EP Application No. 929252529.1.

Berg, Ellen L. et al., A Carbohydrate Domain Common to Both Sialyl Le$^a$ and Sialyl Le$^x$ is Recognized by the Endothelial Cell Leukocyte Adhesion Molecule ELAM-1, *Journal of Biol. Chem.*, vol. 266, No. 23, pp. 14869–4872 (1991).

Nicolaou, K. C., et al. Stereocontrolled Synthesis of Sialyl Le$^x$, the Oligosaccharide Binding Ligand to ElAM-1 (Sialyl=N-acetylneuramin), *J. Chem. Soc., Chem. Commun.*, pp. 870–872 (1991).

Nillson, Marianne et al., Synthesis of Carbohydrate Derivatives Corresponding to a Tumor-Associated Glycolipid: A Trimeric Lewis X Nonasaccharide and a Trimeric N-Acetyl Lactosamine Hexasaccharide, *J. Carbohydrate Chemistry*, pp. 613–627 (1989).

Stanley, Pamela et al., The LEC11 Chinese Hamster Ovary Mutant Synthesizes N-Linked Carbohydrates Containing Sialylated, Fucosylated Lactosamine Units, *Journal of Biological Chemistry*, vol. 263, No. 23, pp. 11374–11381 (1988).

Tiemeyer, Michael et al., Carbohydrate Ligands for Endothelial–Leukocyte Adhesion Molecule 1, *Proc. Natl. Acad. Sci. USA*, vol. 88, pp. 1138–1142 (1991).

Tyrrell, David et al., Structural Requirements for the Carbohydrate Ligand of E-Selectin. *Proc. Natl. Acad. Sci. USA*, vol. 88, pp. 10372–10376 (1991).

Gundel, et al., J. Clin. Invest. 88:1407–1411, 1991.
Mulligen, et al., Nature, 364:149–149–151, 1993.
Mulligen, et al., J. Clin. Invest. 90:1600–1607, 1992.

(List continued on next page.)

*Primary Examiner*—John W. Rollins
*Attorney, Agent, or Firm*—Lyon & Lyon

[57] ABSTRACT

Simple lactose or lactosamine related compounds which behave as ligands for the ELAM-1 and related receptors are described. These compounds are useful in the treatment of conditions characterized by excess inflammation. These compounds are of the formula

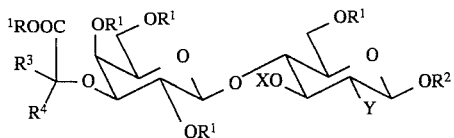

wherein each $R^1$ is independently H or lower alkyl (1–4C);

$R^2$ is H, lower alkyl (1–4C), alkylaryl or one or more additional saccharide residues;

$R^3$ and $R^4$ are each independently H, alkyl(1–6C), aryl or $R^3$ and $R^4$, taken together, form a five- or six-membered ring optionally containing a heteroatom selected from the group consisting of O, S, and $NR^1$;

wherein said five- or six-membered ring may further be substituted by one or more substituents selected from the group consisting of $(CHOR^1)_m H$ wherein m is 1–4, $OR^1$, $OOCR^1$, $NR^1_2$, $NHCOR^1$, and $SR^1$;

Y is H, $OR^1$, $OOCR^1$, $NR^1_2$, $NCOR^1$ or $SR^1$; and

X is $-CHR^5(CHOR^1)_2CHR^6OR^1$ wherein $R^5$ and $R^6$ are each independently H, lower alkyl(1–4C) optionally substituted with one or more F, or result in a five- or six-membered ring optionally containing a heteroatom selected from the group consisting of O, S, and $NR^1$;

said five- or six-membered ring optionally substituted with one substituent selected from the group consisting of $R^1$, $CH_2OR^1$, $OR^1$, $OOCR^1$, $NR^1_2$, $NHCOR^1$, $SR^1$ and F;

or X is benzoyl or naphthoyl having 1–3 hydroxyl substituents, with the proviso that if X represents a hexose substituent $R^3$ and $R^4$, taken together, cannot provide a hexose substituent.

22 Claims, No Drawings

OTHER PUBLICATIONS

Ladisch, et al., J. Clin Invest. 74:2074–2081, 1984.
Khara, et al., Comb. Res. 136:285–308, 1985.
Keilical, et al., Carb. Res. 40:255–262, 1975.
Berg, et al., J. Biol. Chem. 266(23):14869–14872.
Kitagana, et al., B.B.R.C. 178(3):1429–1436, 1991.
Takada, et al. B.B.R.C. 179(2):713–719, 1991.
Hakomori, et al, B.B.R.C. 100(4) 1578–86, 1981.
Gooi, et al., Nature 292:156–8, 1981.
Shur, J. Biol. Chem. 257(12):6871–8, 1982.
Bird, et al., Devel. Biol. 104:449–460, 1984.
Fenderson, et al., J. Exp. Med. 160:1591–1596, 1984.
Gabius, et al., Anticancer Res, 6:573–851 1986.
Lis et al., Ana. Rev. Biochem. 55:35–67, 1986.
Sato, et al., Carb. Res. 155:C6–C10, 1986.
Fenderson, et al., Devel. Biol. 122:21–34, 1987.
Dasgupta, et al., Carb. Res 177:C13–C17, 1988.
Fenderson, et al Differentiation 38:124–133, 1988.
Kojima, et al., J. Biol. Chem. 264(34):20159–62, 1989.
Eggens, et al., J. Biol. Chem. 264(16):9476–84, 1989.
Gundel et al., "Endothelial Leukocyte Adhesion Molecule–1 Mediates Antigen–induced Acute Airway Inflammation and Late–phase Airway Obstruction in Monkeys," J. Clin. Invest. 88:1407–1411 (1991).
Mulligan et al., "Protective Effect is of Oligosaccharides in P–Selectin≧Dependent Lung Injury," Nature, 364:149–151 (1993).
Mulligan et al., "Neutrophil–dependent Acute Lung Injury," J. Clin. Invest. 90:1600–1607 (992).
Hakomori et al., "The Hapten Structure of a developmentally regulated Glycolipid Antigen (SSEA–1) isolated from human erythrocytes and Adenocarcinoma," Biochem. Biophys. Res. Commun. 100(4):1578–86 (1981).

Gooi et al., "Stage–specific embryonic antigen involves $\alpha 1 \rightarrow 3$ fucosylated type 2 blood group chains," Nature 292:156–158 (1981).

Bird et al., "Oligosaccharides Containing Fucose Linked $\alpha(1-3)$ and $\alpha(1-4)$ to N–Acetylglucosamine Cause Decompaction of Mouse Morulae," Biol. 104:449–60 (1984).

Sato et al., "An efficient approach to O–glycosides through $CuBr_2$ —$Bu_4NBr$ mediated activation of glycosides," Carb. Res. 155:C6–C10 (1986).

Fenderson et al., "The blood group I antigen defined by monoclonal antibody C6 is a marker of early mesoderm during murine embryogenesis," Differentiation 38:124–133 (1988).

Kojima et al., "Specific Interaction between Gangliotriaosylceramide $Gg_3$) and Sialosyllactosylceramide ($G_{m3}$) as a Basis for Specific Cellular Recognition between Lymphoma and Melanoma Cells", J. Biol. Chem. 284(34):20159–62 (1989).

Eggens et al., "Specific Interaction between $Le^x$ and $Le^x$ Determinants," J. Biol. Chem. 264(16):9476–84 (1989).

Ladisch et al., "Modulation of the Immune response by gangliosides," J. Clin. Invest. 74:2074–2081 (1984).

Cavillon et al., "Inhibition of lipopolysaccharide–induced monocyte interleukin 1 secretion by gangliosides," European Journl. of Immunol. 16:1009–1012 (1986).

Khare et al., "The synthesis of monodeoxy derivatives of Lacto–N–biose 1 and N–acetyl–lactosamine to serve as substrates for the differentiation of alpha–L–fucosyl Transferase," Carbohydrate Res. 136:285–308 (1985).

Keilical et al., Carb. Res. 40:255–262 (1975).

Berg et al., J. Biol. Chem. 266(23)14869–14872 (8–1991).

SUBSTITUTED LACTOSE AND LACTOSAMINE DERIVATIVES AS CELL ADHESION INHIBITORS

This application is a continuation of U.S. patent application Ser. No. 07/800,557 filed Nov. 27, 1991, now U.S. Pat. No. 5,326,752.

TECHNICAL FIELD

The invention relates to compounds useful in the treatment of inflammation, allergic reactions, autoimmune diseases, and related conditions. More specifically, the invention concerns substituted lactose and lactosamines that bind to the endothelial leukocyte adhesion molecule-1 (ELAM-1) and to pharmaceutical compositions containing them. The present invention is also directed to synthetic methods useful in obtaining these analogs and other lactosamine and lactose derivatives.

BACKGROUND ART

It is now well established that cellular interactions are at least in part mediated by receptor/ligand interactions. One class of receptors is known to recognize the peptide subsequence "RGD"; other receptors recognize carbohydrate ligands.

One class of receptors that recognize carbohydrate-based ligands mediates the adhesion of circulating neutrophils to stimulated vascular endothelium. This is a primary event of the inflammatory response and appears to be involved as well in allergic and autoimmune responses. Several of the lectin-based receptors that are presumably involved in this process include LECAM-1 (gp90$^{mel}$); gmp-140 (PADGEM) and ELAM-1 (LECAM-2). Of particular interest herein is the ELAM-1 receptor which has been shown to interact with the sialyl-Lewis$^x$ oligosaccharide (NeuAc($\alpha$2,3)Gal($\beta$,4)[Fuc ($\alpha$1,3)]GlcNAc.

U.S. patent application Ser. No. 07/683,458, filed 11 Apr. 1991, now U.S. Pat. No. 5,211,937 assigned to the present assignee and incorporated herein by reference discloses and claims the foregoing minimum tetrasaccharide structure and identifies the groups putatively interactive with the ELAM-1 receptor.

The present invention provides analogs of the sialyl-Lewis$^x$ residue which are agonists or antagonists of the ELAM-1 receptor and related cell adhesion receptors as well as an improved synthetic method to prepare both these analogs and compounds which are derivatives of lactose or lactosamine in general.

DISCLOSURE OF THE INVENTION

The invention provides agonists and antagonists which bind the ELAM-1 receptor or other related cell adhesion receptors and thus modulate the course of inflammation and related responses. In this aspect, the invention is directed to compounds of the formula:

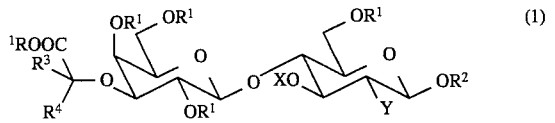

wherein each R$^1$ is independently H or lower alkyl (1–4C);

R$^2$ is H, lower alkyl(1–4C), alkylaryl or one or more additional saccharide residues;

R$^3$ and R$^4$ are each independently H, alkyl (1–6C) or aryl or R$^3$ and R$^4$, taken together, form a five- or six-membered ring optionally containing a heteroatom selected from the group consisting of O, S, and NR$^1$;

wherein said five- or six-membered ring may further be substituted by one or more substituents selected from the group consisting of (CHOR$^1$)$_m$H wherein m is 1–4, OR$^1$, OOCR$^1$, NR$^1{}_2$, NHCOR$^1$, and SR$^1$;

Y is H, OR$^1$, OOCR$^1$, NR$^1{}_2$, NCOR$^1$ or SR$^1$; and

X is —CHR$^5$(CHOR$^1$)$_2$CHR$^6$OR$^1$ wherein R$^5$ and R$^6$ are each independently H, lower alkyl(1–4C) optionally substituted with one or more F, or taken together result in a five- or six-membered ring optionally containing a heteroatom selected from the group consisting of O, S, and NR$^1$;

said five- or six-membered ring optionally substituted with one substituent selected from the group consisting of R$^1$, CH$_2$OR$^1$, OR$^1$, OOCR$^1$, NR$^1{}_2$, NHCOR$^1$, SR$^1$, and F;

or X is benzoyl or naphthoyl having 1–3 hydroxyl substituents, with the proviso that if X represents a hexose substituent R$^3$ and R$^4$, taken together, cannot provide a hexose substituent.

In another aspect, the invention is directed to a method to synthesize lactose and lactosamine derivatives which method comprises contacting an intermediate of the formula

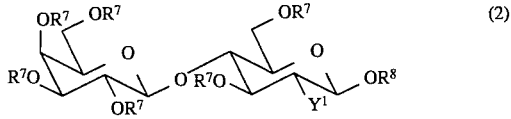

wherein each R$^7$ is independently H, lower alkyl (1–4C), or a protecting group; and wherein Y$^1$ is H, OR$^7$, OOCR$^7$, NR$^{27}$, NCOR$^7$ or SR$^7$;

wherein at least one R$^7$, which is at the position to be substituted, and at most one adjacent R$^7$ is H and all other R$^7$s are protecting groups; and R$^8$ is a protecting group, with an electrophile-donating moiety to obtain a product wherein the electrophile is substituted for the H of the OH at the position to be substituted.

In other aspects, the invention is directed to pharmaceutical compositions containing the compounds of formula 1 and to methods of treating inflammation using these compositions. In other aspects, the invention is directed to compounds of formula 2 and additional intermediates in the synthesis of ELAM-1 binding ligands or other useful lactosyl residue-containing moieties.

MODES OF CARRYING OUT THE INVENTION

The invention provides compounds that are useful in the treatment of inflammation by virtue of their ability to bind to ELAM-1 receptor. Blood vessels are lined with endothelial cells capable of producing the ELAM-1 surface receptor. Lymphocytes circulating in the vessel contain on their surfaces carbohydrate ligands capable of binding to the ELAM-1 receptor. This results in transfer of the lymphocyte through the vessel wall and into the surrounding tissue. While this may have a useful effect in some circumstances, as in cases when the surrounding tissue is infected, excessive transfer of the lymphocytes through the vessel wall and into the tissue cause unwanted inflammation. While not wishing to be limited by any particular theory, it is believed that the compounds of the present invention which bind the ELAM-1 receptor antagonize the action of the surface ligands on the circulating lymphocytes and thus prevent the transfer of these lymphocytes through the blood vessel wall to cause inflammation in the surrounding tissue.

A convenient assay for the ability of the compounds of formula 1 to prevent or control inflammation is provided by cells which have been modified to contain recombinant expression systems for the ELAM-1 receptor. The complete nucleotide sequence encoding ELAM-1 and the amino acid sequence thereof are provided by Bevilacqua, M. P. et al., *Science* (1989) 243:1160. Complete cDNA for the receptor was obtained by PCR starting with mRNA isolated from IL-1 stimulated human umbilical vein endothelium; the recovered cDNA was inserted into CDM8 (Aruffo, A. et al., *Proc Natl Acad Sci USA* (1987) 84:8573) and the plasmid was amplified in *E. coli.* Plasmid DNA from individual colonies was isolated and used to transfect Cos cells. Positive plasmids were selected by their ability to generate Cos cells that support HL-60 cell adhesion; DNA sequencing positively identified one of these clones as encoding ELAM-1.

Cos cells expressing membrane-bound ELAM-1 are metabolically radiolabeled with $^{32}P$ phosphate and used as probes in an assay system to determine the ability of candidate compounds to bind ELAM-1. The candidate compound is adsorbed to PVC microtiter wells and probed with the labeled ELAM-transfected Cos cells or controls under conditions of controlled detachment force as described by Swank-Hill, P. et al., *Anal Biochem* (1987) 183:27 and Blackburn, C. C. et al., *J Biol Chem* (1986) 261:2873, both of which are incorporated herein by reference.

Thus, any candidate compound of the formula 1 may be verified to bind ELAM-1 receptors by a positive result in the foregoing assays. These assays provide a simple screen for determining the relative effectiveness of the various members of the group consisting of compounds of formula 1.

Nontherapeutic Uses of Compounds of Formula 1

In addition to their use in treating or preventing inflammation as is further described hereinbelow, the compounds of formula 1 are useful in diagnostic and preparatory procedures both in vitro and in vivo.

Compounds of formula 1 may be conjugated to solid substrates and used for the purification of ELAM-1 receptor protein from biological samples. This purification is conducted most conveniently by arranging the coupled substrate as an affinity chromatography column and applying a sample putatively containing the ELAM-1 receptor protein to the affinity column under conditions wherein the ELAM-1 receptor protein is adsorbed whereas contaminating materials are not. The ELAM-1 receptor protein is then subsequently eluted, for example, by adjusting the eluent solution to contain competing amounts of the compound of formula 1 or by adjusting pH or salt parameters. Techniques for affinity purification are well understood, and routine optimization experiments will generate the appropriate conditions for conducting of the procedure.

The compounds of formula 1 are also useful as detection reagents to determine the presence or absence of ELAM-1 or related carbohydrate-binding receptor ligands. For use in such diagnostic assays, a biological sample suspected to contain ELAM-1 receptor protein or a receptor protein closely related thereto is treated with the compound of formula 1 under conditions wherein complexation occurs between the receptor protein and the formula 1 compound, and the formation of the complex is detected. A wide variety of protocols may be utilized in such procedures, analogous to protocols applied in immunoassays. Thus, direct assay wherein the amount of complex formed is directly measured may be utilized; alternatively, competition assays may be used wherein labeled ELAM receptor protein is supplied along with, and in competition with, the biological sample. In some forms of the assay, it is convenient to supply the compounds of formula 1 in labeled form so that the complex is detected directly; in alternate procedures, the complex may be detected by size separations, secondary labeling reagents, or other alternate means. Suitable labels are known in the art, and include radioactive labels, fluorescent labels, enzyme labels, chromogenic labels, or composites of these approaches.

The compounds of formula 1 may also be used as competitive diagnostic reagents to detect the quantity of ELAM-1 receptor-binding components, such as surface ligands, in biological fluids. To conduct such assays, the compounds of formula 1 are labeled as described above, mixed with the biological sample and contacted with the appropriate receptor protein; the diminution of binding of the labeled compound of formula 1 to ELAM-1 receptor in the presence of biological sample is then determined.

The compounds of formula 1 may also be used in imaging studies in vivo to determine the location of ELAM-1 receptors in situ. For use in such assays, the compounds of formula 1 are supplied with labels which can be detected by in vivo imaging techniques, such as scintigraphic labels including indium 111, technetium 99, iodine 131, and the like.

Techniques for coupling compounds such as those of formula 1 to labels, chromatographic supports, or other moieties useful in employing the compounds in the relevant procedures are well understood in the art.

Antibodies may also be prepared to the compounds of formula 1 by coupling these compounds to suitable carriers and administering the coupled materials to mammalian or other vertebrate subjects in standard immunization protocols with proper inclusion of adjuvants. Suitable immunogenic carriers include, for example, Keyhole Limpet Hemocyanin (KLH), tetanus toxoid, various serum albumins such as bovine serum albumin (BSA) and certain viral proteins such as rotaviral VP6 protein. These coupled materials are then administered in repeated injections to subjects such as rabbits, rats or mice and antibody titers monitored by standard immunoassay techniques. The resulting antisera may be used per se or the antibody-secreting cells generated by the immunization may be immortalized using standard techniques and used as a source of monoclonal preparations which are immunoreactive with the compounds of formula 1. The resulting antibodies are useful in assay systems for determining the presence and/or amount of the relevant formula 1 compound. Such assays are useful in monitoring the circulating levels of compounds of formula 1 in therapeutic treatments such as those described below.

Administration in Antiinflammatory Protocols

The compounds of the invention are administered to a subject in need thereof for prophylactically preventing inflammation or relieving it after it has begun. "Treating" as used herein means preventing or ameliorating inflammation and/or symptoms associated with inflammation. The compounds are preferably administered with a pharmaceutically acceptable carrier, the nature of the carrier differing with the mode of administration, for example, oral administration, usually using a solid carrier and I.V. administration using a liquid salt solution carrier. Typically, injectable compositions are prepared as liquid solutions or suspensions; solid forms suitable for solution in, or suspension in, liquid vehicles prior to injection may also be prepared. The compounds may also be emulsified or the active ingredient encapsulated in liposome vehicles.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, for example, *Remington's Pharmaceutical Sciences,* Mack Publishing Company, Easton, Pa., 17th edition, 1985.

Formulations may employ a variety of excipients including, for example, pharmaceutical grades of mannitol, lactose, starch, magnesium stearate, lo sodium saccharin cellulose, magnesium carbonate, and the like. Oral compositions may be taken in the form of solutions, suspensions, tablets, pills, capsules, sustained release formulations, or powders. Particularly useful is the administration of the subject ligand molecules directly in transdermal formulations with permeation enhancers such as DMSO. Other topical formulations can be administered to treat dermal inflammation. In addition, transmucosal administration may be effected using penetrants such as bile salts or fusidic acid derivatives optionally in combination with additional detergent molecules. These formulations are useful in the preparation of suppositories, for example, or nasal sprays. For suppositories, the vehicle composition will include traditional binders and carriers, such as polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

In determining the dose to be administered, it will be noted that it may not be desirable to completely block all ELAM-1 receptors. In order for a normal healing process to proceed, at least some of the white blood cells or neutrophils must be brought into the tissue in the areas where any wound, infection or disease state is occurring. The amount of the ELAM-1 ligands administered as blocking agents must be adjusted carefully based on the particular needs of the patient while taking into consideration a variety of factors such as the type of disease that is being treated.

The compounds of the present invention are useful to treat a wide range of diseases, for example autoimmune diseases such as rheumatoid arthritis and multiple sclerosis. The compositions of the invention are applicable to treat any disease state wherein the immune system turns against the body causing the white cells to accumulate in the tissues to the extent that they cause tissue damage, swelling, inflammation and/or pain.

Formulations of the present invention might also be administered to prevent the undesirable after effects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated endothelial cells then synthesize the ELAM-1 receptors within hours of the cells being damaged. The receptors are extended into the blood vessels where they adhere to glycolipid ligand molecules on the surface of white blood cells. Large numbers of white blood cells are quickly captured and brought into the tissue surrounding the area of activated endothelial cells, resulting in inflammation, swelling and necrosis lo which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other conditions treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Applications of Compounds of Formula 2

The compounds of formula 2 are intermediates in the preparation of compounds which contain a lactosyl or lactosamine unit. Notably, the compounds of formula 2 are useful in the preparation of compounds of formula 1 whose use is described hereinabove. In addition to the compounds of formula 1, alternative compounds containing a lactose or lactosamine residue may also be prepared, such as 4-O-(3-O-carboxymethyl-β-D-galactopyranosyl)-3-D-[2R, S)-glyceryl] -D-glucopyranose;

4-O-(3-O-carboxymethyl-β-D-galactopyranosyl)-3-O-[2R, S)-2,3 -dideoxy-2,3-difluoro-propyl]-D-glucopyranose;

4-O-[3-O-{(1 R,S)-1-(carboxy)ethyl}-β-D-galactopyranosyl]-3-O-[(2 R, S)-glyceryl]-D-glucopyranose;

4-O-[3-O-{(1R,S)-1-(carboxy)ethyl}-β-D-galactopyranosyl]-3-O-(α-L-fucopyranosyl)-D-glucopyranose;

4-O-[3-O-(α-Neu5Ac)-β-D-galactopyranosyl]-3-O-[(2R, S)-glyceryl]-D-glucopyranose;

4-O-[3-O-(α-Neu5Ac)-β-D-galactopyranosyl]-3-O-[(2 R,S)-2,3 -dideoxy-2,3-difluoro-propyl]-D-glucopyranose.

Multivalent Forms of the Receptor Binding Ligands

The affinity of the ligands of the invention for receptor can be enhanced by providing multiple copies of the ligand in close proximity, preferably using a scaffolding structure provided by a carrier moiety. It has been shown that provision of such multiple valence structures with optimal spacing between the moieties dramatically improves binding to receptor. For example, Lee, R. et al., *Biochem* (1984) 23:4255, showed that providing multivalent forms of lactose inhibited labeled ASOR binding to mammalian hepatocytes much more effectively when the lactose was supplied as a multivalent entity; the $IC_{50}$ dropped from 500 μM for a monovalent lactose to 9 for a divalent lactosyl compound to 4 for a trivalent lactosyl compound, and with ideal or optimal spacing between the three lactose moieties to 0.007 μM.

The multivalency and spacing can be controlled by selection of a suitable carrier moiety. Such moieties include molecular supports which contain a multiplicity of functional groups that can be reacted with functional groups associated with the ligands of the invention. A particularly preferred approach involves coupling of the lactose-derived ligands of the invention to amino groups of the carrier through reductive amination. Reductive amination is a particularly convenient way to couple aldehyde moieties to free amino groups by first forming the Schiff base and then treating the conjugate with a reducing agent, such as a hydride reducing agent. Typically, the amino group-bearing carrier is mixed with the carbohydrate moiety at about pH 9 and allowed to form the Schiff base; the solvents are typically evaporated and reducing agent is added at high pH to complete the reaction.

Particularly convenient carrier moieties to obtain multivalent forms of the invention ligands include proteins and peptides, particularly those containing lysyl residues which have s-O-amino groups available for binding. It is also useful to include in the peptide or protein at least one tyrosine residue, as this offers a convenient site for labeling, for example with radioactive iodine. A particularly convenient carrier to obtain a trivalent couple is the peptide Lys-Tyr-Lys. Complete reaction of the ligands of the invention with the free amino groups on this peptide result in a trivalent moiety. Thus, compounds of the invention of the formula course, a variety of carriers can be used, including proteins such as BSA or HSA, a multiplicity of peptides including, for example, pentapeptides, decapeptides, pentadecapeptides, and the like. Preferably, the peptides or proteins contain the desired number of amino acid residues having free amino groups in their side chains; however, other functional groups, such as sulfhydryl groups or hydroxyl groups can also be used to obtain stable linkages. For example, the carbohydrate ligands of the invention may be oxidized to contain carboxyl groups at the reducing terminus which can then be derivatized with either free amino groups to form amides or with hydroxyl groups to form esters.

Preparation of the Compounds of Formula 1

The compounds of the invention of Formula 1 may be synthesized using an intermediate of Formula 2. The intermediate of Formula 2, in one embodiment, can be prepared directly from D-lactose using standard procedures. In this conversion, D-lactose is converted to the octaacetate in crystalline form, in over 95% yield in the method described by Hudson, C., and Kuns, A., *J Am Chem Soc* (1925) 47:2052. The octaacetate is, in turn, converted in more than 90% yield by the method of Hudson, C. (supra) or of Fischer, E. and Fischer, H., *Ber* (1910) 43:2521 to the corresponding lactosyl bromide, also a crystalline compound. The protected lactosyl bromide is converted by the method of Jansson, K., et al., *J Org Chem* (1988) 53:5629, in over 60% yield to the corresponding acylated trimethylsilyl ethyl lactose, which can be deprotected by deacylation in quantitative yield to obtain 2-(trimethylsilyl)ethyl lactose—i.e., 2-(trimethylsilyl)ethyl β-D-galactopyranosyl-β-D glucopyranoside. Alternative protective groups at position 1 of the disaccharide may also be used.

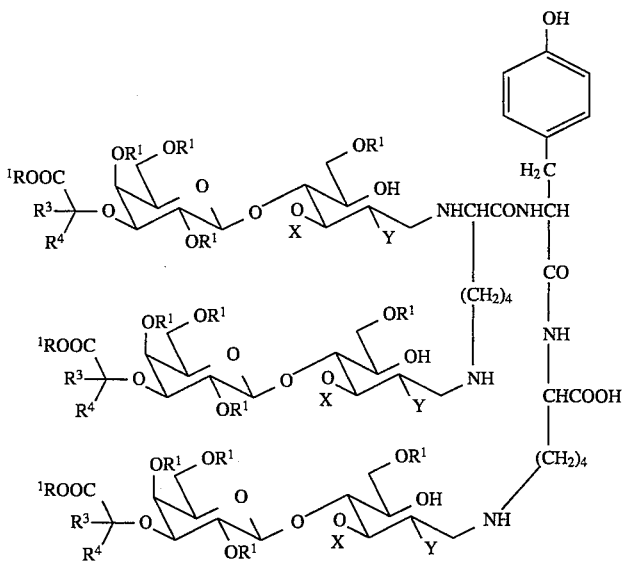

(3)

wherein X, Y, and $R^1$, $R^3$ and $R^4$ are as defined above illustrate the multivalent compounds of the invention. Of This precursor of the compounds of Formula 2 is of the formula:

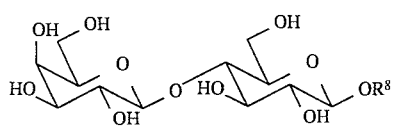

5 wherein R[8] is a protecting group, preferably SE or Bn, wherein SE represents —CH$_2$CH$_2$SiMe$_3$ and Bn is benzyl.

Reaction Scheme 1 outlines the formation of one embodiment of the compounds of Formula 2 from this intermediate, where Bz represents benzoyl.

In step 1 of the reaction scheme, the protected lactose, e.g., the trimethylsilyl ethyl derivative or benzyl derivative, is treated with an excess of 2,2-dimethoxypropane and dry camphor sulfonic acid is added to the reaction mixture which is stirred for 2–3 days at about room temperature. A suitable base, such as triethylamine is added and stirring continued for 10–20 minutes; the mixture is then concentrated to dryness and the base removed. The reaction mixture is worked up using standard procedures to recover the product 6. This intermediate is then benzoylated under suitable conditions using, for example, benzoyl chloride to obtain the intermediate compound shown in reaction scheme as 7.

The intermediate 7 may then be further derivatized at the free hydroxyl at the 3-position of the glucoside residue or this position may be protected and the compound deprotected at positions 3 and 4 of the galactosyl residue and further derivatized at position 3. Position 4 of the galactosyl residue is relatively unreactive. Typical schemes for utilization of this key intermediate 7 are shown in Reaction Schemes 2A and 2B. (In these depictions, Bz is benzoyl (PhCO—) and Bn is benzyl (PhCH$_2$—).

Reaction Scheme 1

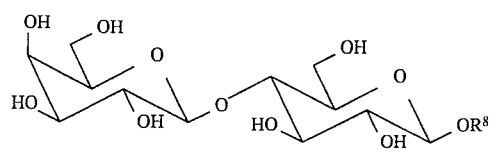

5

Step 1 | 88%, Flash Chromatography

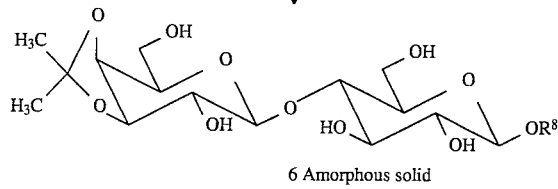

6 Amorphous solid

Step 1 | 6a R[8] = SE
        | 6b R[8] = Bn

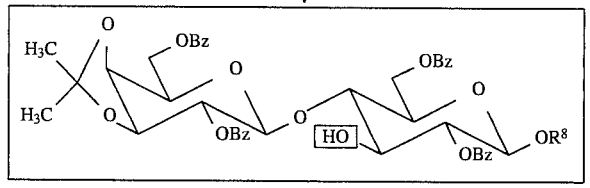

7
7a R[8] = SE
7b R[8] = Bn

Reaction Scheme 2A

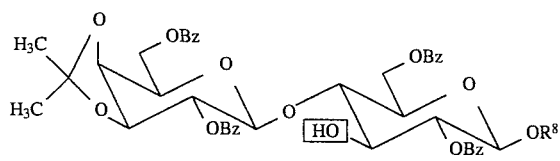

7

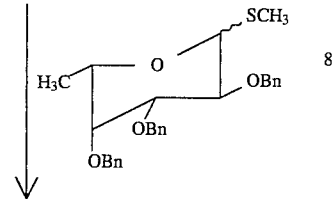

8

-continued
Reaction Scheme 2A
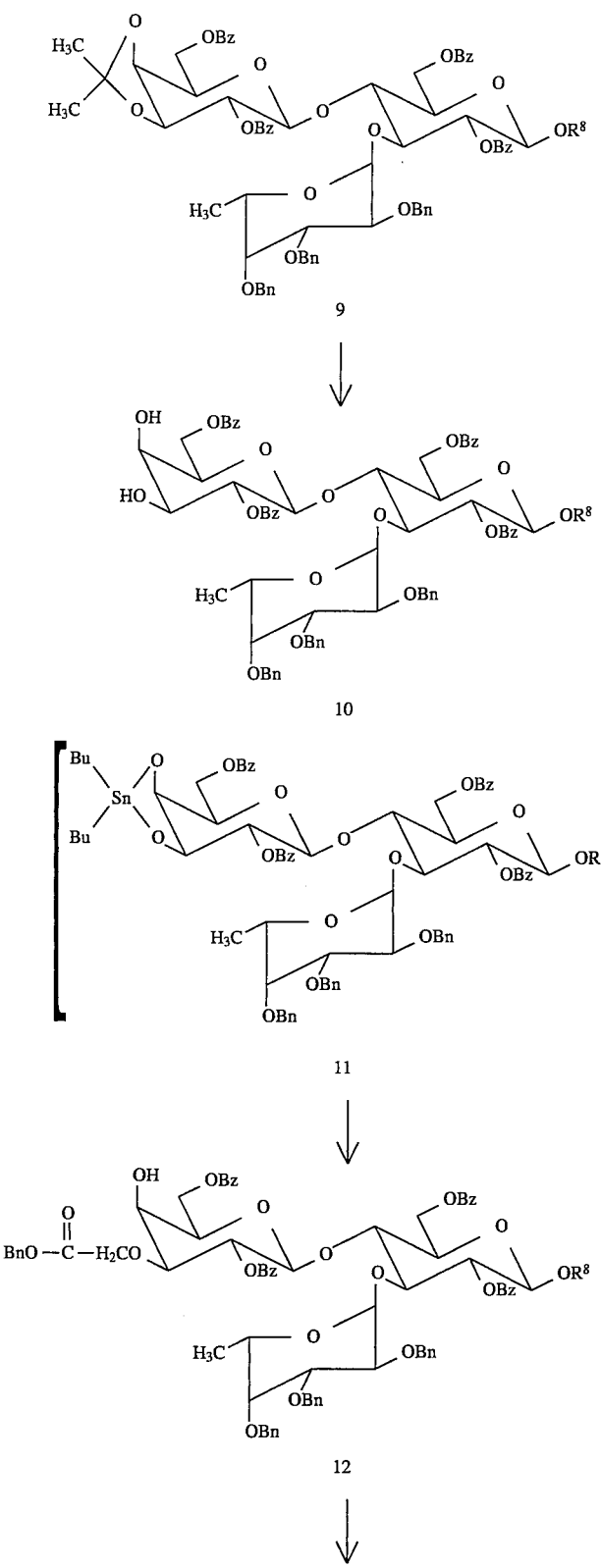

-continued
Reaction Scheme 2A

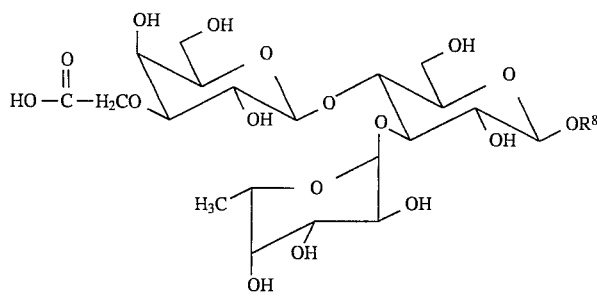

13

As shown in Reaction Scheme 2A, the intermediate 7 is converted in two steps to intermediate 10 by treatment under suitable conditions with protected methyl 1-thio-L-fucoside. The reaction is conducted in a nonaqueous aprotic solvent in the presence of cupric bromide, tetrabutylammonium bromide and molecular sieve. The resultant compound shown as 10 having free OH groups in positions 3 and 4 of the galactosyl residue is then reprotected by treatment using dibutyl tin oxide in the second step of Reaction Scheme 2A, resulting in the intermediate shown as 11, which is not isolated. This reaction is conducted in methanol under reflux with the protecting reagent, as described by Nashed, M. A. et al., *Tet Lett* (1976) 39:3503–3506.

The resulting intermediate 11 is then converted in situ to a preferred form of the compound of Formula 1 in two steps, also shown in scheme 2A. The dibutyl tin is replaced by any desired electrophile at position 3 of the galactosyl residue and the intermediate 12 converted to the final preferred product 13. This conversion is effected by treating 12 in methanol in the presence of palladium charcoal catalyst followed by treatment with base to remove the protecting groups.

Alternatively, the intermediate 7 can be derivatized initially at the position occupied by the isopropylidene group as shown in Reaction Scheme 2B.

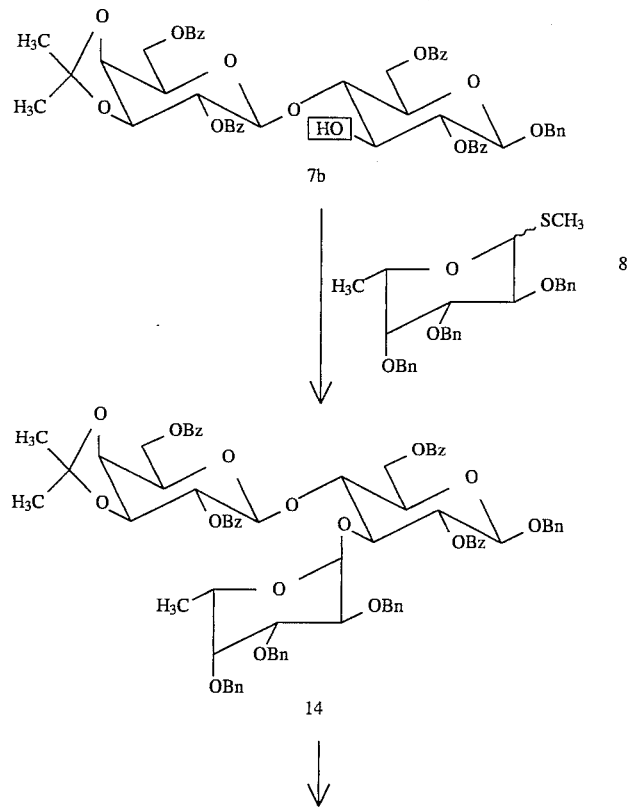

Reaction Scheme 2B

-continued
Reaction Scheme 2B
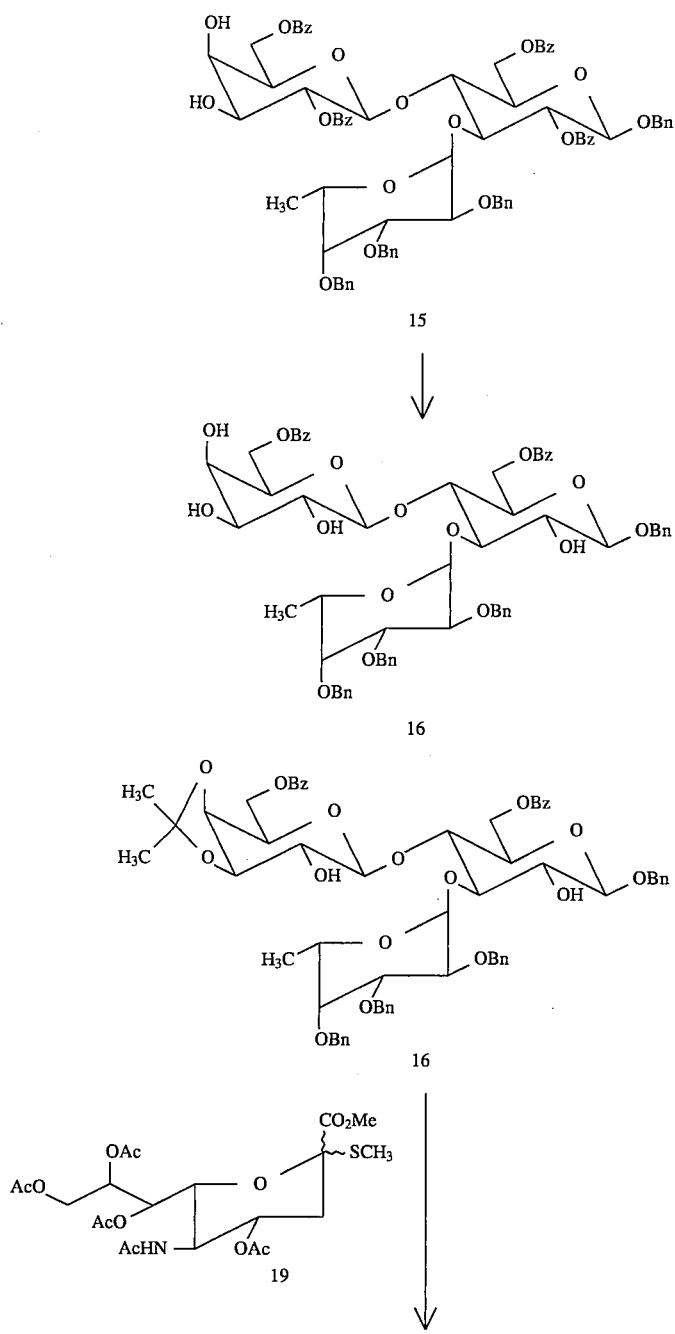

-continued
Reaction Scheme 2B

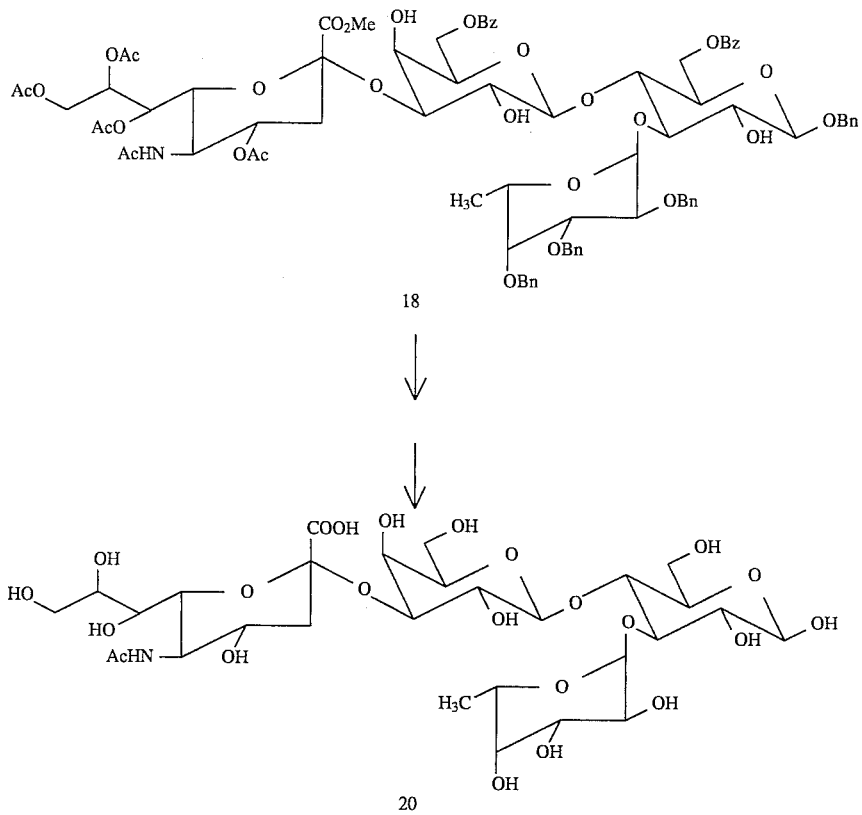

The sequence of reactions set forth in Scheme 2B is generally as disclosed by Sato, S. et al. *Carbohydrate Res* (1986) 155:C6–C10; Dasgupta, F. and Garegg, P. J., *Carbohydrate Res* (1988) 177:C13–C17. As shown in Scheme 2B, the benzoyl-protected key intermediate is first reacted with the thiofucoside to obtain the trisaccharide 14. Debenzoylation of the intermediate provides intermediate 15, which is converted by selective benzoylation to the partially protected trisaccharide 16. Further hydrolysis of the isopropylidene group provides the trisaccharide 17, which is then reacted with the acylated methylthiolated sialyl residue to obtain 18; the intermediate 18 may then be lo deprotected to obtain the final product 20.

Compounds of the Invention and Preferred Embodiments

As used herein, alkyl (1–6C) refers to a saturated straight or branched chain or cyclic hydrocarbyl residue containing 1–6C; lower alkyl is similarly defined but containing only 1–4C.

As used herein, alkylaryl is of the formula $(CH_2)_m$—Ar wherein m is 1–10 and Ar is a mono- or bicyclic aromatic residue optionally containing one or more heteroatoms. Typical embodiments of Ar include phenyl, naphthyl, quinolyl, pyridyl, pyrimidinyl, benzthiazoyl, benzimidazoyl, and the like.

$R_8$ is a protecting group suitable for saccharide residues. Typical protecting groups include benzyl, benzoyl, various silylalkyl groups, such as trimethylsilylethyl (SE), and the like.

Exemplary compounds of formula 1 of the invention are those wherein $R^3$ and $R^4$ taken together are:
3,4,5-trihydroxypyran-2-yl,
3,4,5-trimethoxypyran-2-yl,
3,4,5-trimethoxymethylpyran-2-yl,
3,4,5-triacetylpyran-2-yl,
3,4,5-tri-N-propylaminopyran-2-yl,
3,4,5-tri-N,N-dibutylaminopyran-2-yl,
3,4,5-tripropylamidopyran-2-yl,
3,4,5-trimethylthiopyran-2-yl,
4,5-dihydroxypyran-3-yl,
4,5-dimethoxypyran-3-yl,
4,5-dimethoxymethylpyran-3-yl,
4,5-diacetylpyran-3-yl,
4,5-di-N-propylaminopyran-3-yl,
4,5-di-N,N-dibutylaminopyran-3-yl,
4,5-dipropylamidopyran-3-yl,
4,5-dimethylthiopyran-3-yl,
3,4,5-trihydroxypiperidin-2-yl,
3,4,5-trimethoxypiperidin-2-yl,
3,4,5-trimethoxymethylpiperidin-2-yl,
3,4,5-triacetylpiperidin-2-yl,
3,4,5-tri-N-propylaminopiperidin-2-yl,
3,4,5-tri-N,N-dibutylaminopiperidin-2-yl,
3,4,5-tripropylamidopiperidin-2-yl,
3,4,5-trimethylthiopiperidin-2-yl,
3,4,5-trihydroxypyridine-2-yl,
3,4,5-trimethoxypyridine-2-yl,
3,4,5-trimethoxymethylpyridine-2-yl,
3,4,5-triacetylpyridine-2-yl,
3,4,5-tri-N-propylaminopyridine-2-yl,
3,4,5-tri-N,N-dibutylaminopyridine-2-yl,
3,4,5-tripropylamidopyridine-2-yl,
3,4,5-trimethylthiopyridine-2-yl, 4,5-dihydroxythiazol-2-yl,
4,5-dimethoxythiazol-2-yl,
4,5-dimethoxymethylthiazol-2-yl,
4,5-diacetylthiazol-2-yl,
4,5-di-N-propylaminothiazol-2-yl,
4,5-di-N,N-dibutylaminothiazol-2-yl,
4,5-dipropylamidothiazol-2-yl,
4,5-dimethylthiothiazol-2-yl,
2-hydroxy-4-methoxyfuran-3-yl,
2-acetyl-4-N-propylfuran-3-yl,
2-propylamido-5-methylthiofuran-3-yl,
2,4-diethoxymethylfuran-3-yl,
4-N,N-dibutylaminofuran-3-yl; and
2-propanoylfuran-3-yl; or wherein one of $R^3$ or $R^4$ is H and the other is
methyl,
ethyl,
n-butyl,
phenyl,
pyridin-2-yl, or wherein both $R^3$ and $R^4$ are H; or wherein both $R^3$ and $R^4$ are methyl or ethyl.

Additional exemplary compounds of formula 1 include those wherein X is:
6-methyl-3,4,5-trihydroxypyran-2-yl,
6-acetyl-3,4,5,trihydroxypyran-2-yl,
6-propylamido-3,4,5,trihydroxypyran-2-yl,
6-propylamido-2,3,4-trimethoxypyran-2-yl,
6-ethyl-2,3-dihydroxy-4-methoxypyran-2-yl,
6-N-ethylamino-2-hydroxy-3,4-ethoxypyran-2-yl,
3,4,5-tri-n-propyloxypyran-2-yl,
3,4,5-trihydroxypyran-2-yl,
2,3,4-trimethoxyfuran-2-yl,
2,3-dihydroxy-4-methoxyfuran-2-yl,
2-hydroxy-3,4-ethoxyfuran-2-yl,
3,4,5-tri-n-propyloxyfuran-2-yl, and
3,4,5-trihydroxyfuran-2-yl;

or wherein both $R^5$ and $R^6$ are H and all $R^1$ in X are H or methyl;

or wherein X is 2,3,4-trihydroxybenzoyl.

Thus, particularly preferred compounds of formula 1 are those wherein all $R^1$ are H or methyl, Y is H, OH, OCH$_3$ or OAc; and/or X is —CH$_2$(CHOH)$_3$H, 3,4,5-trihydroxypyran-2-yl, 3,4,5-trihydroxy-6-methylpyran-2-yl, 3,4,5-trimethoxypyran-2-yl, 3,4,5-trimethoxy-6-methylpyran-2-yl, 3,4,5-trihydroxyfuran-2-yl, 3,4,5-trimethoxyfuran-2-yl, 2,3,4-trihydroxybenzoyl, or 2,3,4-trihydroxynaphthoyl; and/or one of $R^3$ and $R^4$ is H and the other is H or lower alkyl or phenyl; or wherein $R^3$ and $R^4$ taken together represent a 3,4,5-trihydroxypyran-2-yl derivative.

Most preferred of the compounds of formula 1 are those wherein all $R^1$ are H, $R^2$ is H, Y is H or OH, X is 3,4,5-trihydroxybenzoyl, —CH$_2$(CHOH)$_3$H, or a 3,4,5-trihydroxypyran-2-yl moiety.

For those compounds of formula 2 which represent intermediates preferred forms are those wherein the protecting groups represented by $R^7$ are benzyl or benzoyl, the protecting group represented by $R^8$ is trimethylsilylethyl or benzyl, and wherein $Y^1$ is H, OR$^7$ wherein R$^7$ is benzyl or benzoyl as set forth above, and where the free hydroxyl is at position 3 of the glucosyl moiety or positions 3 and 4 of the galactosyl moiety. An additional preferred protecting group for positions 3 and 4 of the galactosyl moiety is isopropylidene.

The following examples are intended to illustrate but not to limit the invention.

Preparation A

Preparation of 2-(Trimethylsilyl) ethyl 4-O-(3,4-O-isopropylidene-β-D-galactopyranosyl)-β-D-glucopyranoside(6a)

To a solution of 5 wherein $R^8$ is SE, (14.8 g, 33.5 mmol) in 2,2-dimethoxypropane (270 mL) was added dry camphorsulfonic acid (300 mg). The mixture was stirred for 48 hr at room temperature. Triethylamine (2.3 mL) was added and the mixture was stirred for 15 min. The mixture was then concentrated to dryness and toluene was evaporated from the residue to remove traces of triethylamine. A solution of the crude product in 10:1 MeOH:H$_2$O (350 mL) was boiled under reflux for 3 hr. The solvents were evaporated off, and the residue was flash chromatographed (chloroform:methanol, 19.5:0.5) to give the title compound 6a (14g, 86.7%), [α]$_D$ (Magnusson et al., *J Org Chem* (1988) 53:5629–5647)=[α]$_D$+6°; positive ion LSIMS:m/z 483.5 (M+H$^+$), 505.4 (M+Na)$^+$, 615.3 (M+Cs)$^+$; negative ion, m.s.:481.4 (M–H$^+$); 528.4 (M+NO$_2$); 635.2 (M+m–NBA).

EXAMPLE 1

Preparation of 2-(Trimethylsilyl) ethyl 2,6-di-O-benzoyl-4-O-(2,6 -di-O-benzoyl-3,4-O-isopropylidene-β-D-galactopyranosyl)-β-D-glucopyranoside (7 a)

Compound 6a (13.2 g, 2.74 mmol) was dissolved in dry pyridine (200 mL), the solution was stirred, cooled to –45° C., and benzoyl chloride (14.0 mL, 119.5 mmol) was added dropwise. The reaction mixture was stirred at –45° C. for further 4 hr, at which time t.l.c. (toluene:ethylacetate, 8.5:1.5) showed a single, major product and two minor components, only one of which (pentabenzoate) moved faster than the major component. The reaction mixture was poured into ice-water, extracted with dichloromethane, washed successively with sodium hydrogen carbonate solution and water, dried, and then evaporated. The residue was purified on a column of silica gel furnished an amorphous solid compound 7a (17.29, 66%) which crystallized from hot methanol, needles, $^1$H NMR gives the predicted peaks.

EXAMPLE 2

Preparation of 2-(Trimethylsilyl) ethyl 3-O-(2,3,4-tri-O-benzyl-L-fucopyranosyl)- 4-O-(2,6-di-O-benzoyl-β-D-galactopyranosyl)-2,6-di-O-benzoyl-β-D-glucopyranoside 10(a)

Intermediate 7a, (3.4 g, 3.78 mmol) was dissolved in dry dichloromethane:DMF (5:1,50 mL) and tetrabutylammonium bromide (260 mg), cupric bromide (1.6 g), and powdered 4-Å molecular sieves (2 g) were added. The reaction mixture was stirred at room temperature under argon for two hrs, methyl 2,3,4-tri-O-benzyl-1-thio-L-fucoside (2.2 g) was then added, and the mixture was stirred for 48 hr. Purification of the crude coupling product on a column of silica gel afforded 4.15 g (83.5%) of pure fully protected trisaccharide, $^1$H NMR give the expected pattern positive ion LSIMS:1313.8 (M+1)$^+$, negative ion LSIMS:1361.2 (M+NO$_2$), and 1466.3 (M+m–NBA).

The trisaccharide derivative was treated with aq. acetic acid 70% (30 mL) at 80° C. for ~4 hr at which time t.l.c. (toluene:EtOAc, 8:2) showed no starting material was left. The solvents were removed and toluene was evaporated from the residue to remove the acetic acid, and the residue was chromatographed on a column of silica gel to give 400 mg (69%) of the title compound 10a as an amorphous solid; $^1$H NMR was as expected.

EXAMPLE 3

Preparation of 2-(Trimethylsilyl)ethyl 3-O-(2,3,4-tri-O-benzyl-β-L-fucopyranosyl)- 4-O-(2,6-di-O-benzoyl-3-O-benzyl ethanoate-β-D-galactopyranosyl)- 2,6-di-O-benzoyl-β-D-glucopyranoside 2a)

A solution of compound 10a (150 mg) in methanol (10 mL) was heated for 30 min under reflux with dibutyl tin oxide (50 mg). The methanol was evaporated off and the residual solid was dried with a vacuum pump for ~1 hr. A solution of the solid in dry benzene contains MS 4 Å (100 mg), and tetrabutylammonium bromide (40 mg) was then stirred at room temperature for -30 min and bromoacetic acid (benzyl ester) (0.1 mL) was added. The reaction mixture was heated at 90° C. for ~1 hr, at which time t.l.c. (toluene:EtOAc, 8.5:1.5) showed complete conversion of the starting material into a product having higher mobility. Volatile materials were removed by evaporation under diminished pressure, and the residue was chromatographed on a column of silica gel to give 150 mg (~90%) of the title compound 128 as a syrup; $^1$H NMR (CDCl$_3$); similar to that of 10a except for an additional signal at δ5.31 (q, 2 H$_1$—OCH$_2$—COOH).

EXAMPLE 4

Preparation of 2-(Trimethylsilyl) ethyl 3-O-(α-L-fucopyranosyl)-4-O-( 3-O-carboxymethyl-β-D-galactopyranosyl)-β-D-glucopyranoside (13a)

Compound 12a (50 mg) in methanol (10 mL) was treated with 10% palladium/charcoal catalyst (~100 mg), and the suspension was stirred overnight under hydrogen at 50 lb/sq. inch. The catalyst was removed, and the solution was treated with sodium methoxide (~30 mg) to remove the benzoyl groups. The solution was neutralized with Amberlite IR-120(H$^+$) resin, and filtered. The resin was washed with 1:1 water:methanol, and the combined filtrate and washings were concentrated to a syrup that was chromatographed on a column of Sephadex LH-20 (15 g) with 3:7 water:methanol, to give the title compound 13a (18 mg, 82%) as an amorphous mass. $^1$H NMR (D$_2$O): as expected; negative ion LSIMS: 645.6 (M–H$^+$).

EXAMPLE 5

Preparation of Benzyl 2,6-di-O-benzoyl-4-O-(2,6-di-O-benzoyl- 3,4-O-isopropylidene-β-D-galactopyranosyl)-β-D-glucopyranoside (7b)

A stirred and cooled (–45° C. bath) solution of compound 6b (5g, 10.6 mmol; D. Beith-Halahmi et al., *Carbohydr Res* (1967) 5:25) was treated with benzoyl chloride (6 mL, 51.8 mmol), dropwise, and the stirring was continued for 4 h at –45° C. Processing as described for 6a, followed by column chromatography and recrystallization from hot methanol, afforded 7b (5.53g, 59%), m.p. 159°–161°, [α]$_D$–4.20 (c, 1.3, chloroform). The $^1$H-NMR of this compound contained signals in support of the structure assigned.

EXAMPLE 6

Preparation of BenzylO-(2,3,4-tri-O-benzyl-α-L-fucopyranosyl)-(1-3-[O-( 2,6-di-O-benzoyl-3,4-O-isopropylidene-β-D-galactopyranosyl)-(1–4)]- 2,6-di-O-benzoyl-62 -D-glucopyranoside (9b)

A mixture of compound 7b (4g, 4.5 mmol), methyl 2,3,4-tri-O-benzyl- 1-thio-α-L-fucopyranoside (3.6g, 7.75 mmol) and powdered 4 A molecular sieves (10g), in 5:1 dichloroethane-N,N-dimethylformamide (120 mL), protected from moisture, was stirred for 2 h at room temperature. Cupric bromide (2g, 9 mmol), and tetrabutylammonium bromide (0.29g, 0.9 mmol) were added and the stirring was continued for 35 h at room temperature. More of the donor thiofucoside (1.2 g, 2.6 mmol, in 14.4 mL of the solvent mixture), cupric bromide (0.67 g, 0.3 mmol), and molecular sieves (2 g) were added, and the stirring was continued for an additional 16 h at room temperature. After customary processing, the mixture was purified in a column of silica gel using 5% ethyl acetate in toluene as the eluant. On concentration, the fractions corresponding to the product gave a solid residue, which crystallized from ether to afford 9b (3.68 g, 76%, based on reacted 71;2). Compound 7b (0.7 g) was recovered unchanged. Compound 9b had m.p.180°–181°, [α]$_D$–8° (c, 1.1, chloroform).

EXAMPLE 7

Benzyl 2,6-di-O-benzoyl-3-O-(2,3,4-tri-O-benzyl-α-L-fucopyranosyl)-4-O-( 2,6-di-O-benzoyl-3,4-O-isopropylidene-β-D-galactopyranosyl)-β-D-glucopyranoside (14)

Compound 7b (2.15 g, 2.39 mmol) was dissolved in 5:1 dichloroethane-N,N-dimethylformamide (48 mL) and stirred (2 h) in the presence of molecular sieve 4A (2 g), tetrabutyl ammonium bromide (0.175 g, 0.54 mmol) and cupric bromide (0.975 g, 4.36 mmol). A solution of methylthio-2,3,4-tri-O-benzylfucoside (8) (1.7 g, 3.66 mmol) in dichloroethane (2.0 mL) was added into the well-stirred reaction mixture. Stirring was continued (for 2 days) when t.l.c. (20:1 toluene-acetone) indicated complete absence of the acceptor and a major product. The reaction mixture was filtered through Celite; flask and residue were washed with chloroform (2×5 ml) and the total filtrate was washed with aqueous NaHCO$_3$ and water. Drying (anhydrous MgSO$_4$), filtration and concentration of the filtrate afforded a syrup which was charged as a solution in chloroform (3–5 mL), on a silica gel column and eluted with 800:10:1 toluene-acetone-MeOH. Fractions containing 14b were pooled and evaporated to afford pure 141;2 as a syrup (2.32 g, 74%), m.p. (methanol) 180°–181 ° C., [α]$_D$=–0.8°; [α]$_{436}$–1.12° (c 1.9, CHCl$_3$). NMR data: $^{13}$C, δ(CDCl$_3$) 166.00–168.30 (4CO); 112.46 [c(CH$_3$)$_2$], 102.25, 101.87 (c-1, glc and gal), 98.99 (C-1-Fuc).

EXAMPLE 8

Benzyl 3-O-(2,3,-tri-O-benzyl-α-L-fucopyranosyl)- 4-O-(3, 4-O-isopropylidene-β-D-galactopyranosyl)-β-D-glucopyranoside (15)

Compound 14 (0.47 g) was dissolved in dry methanol (50 mL) and a catalytic amount of sodium metal was added into it and deacylation was carried out at 45° C. At the end of the reaction (4 h, t.l.c. 95:5 CH$_2$Cl$_2$—MeOH), the reaction mixture was neutralized with IR 120 (H$^+$) at 5° C., filtered and evaporated to a syrup. This was purified by column chromatography (silica gel eluent). Pure product 15 (0.285 g, 90%) was crystallized form ether-hexane, m.p. 122°–124° C. NMR data: (CHCl$_3$): 1H, ,5 7.40–7.15 (m, 20H, arom.), 597 (d, J 2.7 Hz, 1H, H-1 Fuc), 4.95–4.5 (m, 10H, PhCH$_2$X4, H-5 Fuc, H-1 hexopyranose), 4.38 (d, J 7.7 Hz, 1H, H-1 hexopyranose), 1.36, 1.30 (2S, 6H, (CH$_{32}$C=), and 1.08 (d, J 6.5 Hz, 3H, CH$_3$-Fuc); $^{13}$C, δ110.85 (C(CH$_3$)$_2$), 103.03, 101.75 (C-1, gal and glc), 98.02 (C-1 Fuc), 75.29, 73.26, 72.95, 72.57 (CH$_2$C$_6$H$_5$×4), 63.19, 60.63 (C6-hexopyranose), 28.85, 26.84 [(CH$_3$)$_2$] and 17.52 (CH$_3$-Fuc).

EXAMPLE 9

Benzyl 6-O-benzoyl-3-O-(2,3,4-tri-O-benzyl-α-L-fucopyranosyl)-4-O-(6-O-benzoyl- 3,4-O-isopropylideneβ-D-galactopyranosyl)-β-D-glucopyranoside (16)

Benzoyl chloride (220 μl, 1.29 mmol) was added into a stirred solution of compound 15 (590 mg, 0.54 mmol) in pyridine (40 ml) maintained at −40° C. T.l.c. (4:1:0.1 toluene-acetone-MeOH) after 6 h indicated conversion to one major product. Chloroform (40 ml), followed by crushed-ice water (50 ml), was introduced into the flask. The organic layer was separated, washed a second time with water, dried (anhydrous $MgSO_4$), filtered and evaporated. Repeated coevaporation with toluene removed the pyridine. The crude material was purified by column chromatography to give the name compound 16 (600 mg, 82%). NMR data ($CDCl_3$): $^{13}C$, δ166.86, 166.62 (200), 139.25, 139.12, 137.99, 137.49 (4 C-1 phenyl), 111.20 [$\underline{C}(CH_3)_2$], 101.62, 101.53, 101.36 (3C-1, gal, glc and Fuc), 75.61, 79.65, 72.89, 71.34 (4 $CH_2$-Ph), 64.00, 63.85 (2 C-6, gal, glc), 28.79, 26.89 [($\underline{C}H_3)_2C$] and 17.5 ($CH_3$-Fuc).

EXAMPLE 10

Benzyl 6-O-benzoyl-3-O-(2,3,4-tri-O-benzyl-α-L-fucopyranosyl)-4-O-(6-O-benzoyl-β-D-galactopyranosyl)-β-D-glucopyranoside (17)

Compound 16 (600 mg) was dispersed in aqueous acetic acid (70%, 70 ml) and stirred while being heated at 80° C. (oil bath). After 3 h, t.l.c. (4:1:0.1 toluene-acetone-methanol) indicated complete conversion into a product with lower mobility. Toluene (50 ml) was added and the solvents evaporated off on a rotary evaporator. Repeated coevaporation with toluene removed all acetic acid and afforded compound 17 as a foam (500 mg, 86%), $[\alpha]_D$ −41.6°; $[\alpha]_{436}$ −820 (c 2.6; $CHCl_3$).

EXAMPLE 11

Benzyl O-(Methyl 4,7,8,9-tetra-O-acetyl-5-acetamido-3,5-dideoxy-D-glycero-α-D-galacto-2-nonulopyranosonate)-(2→3)-O-(6-O-benzoyl-β-D-galactopyranosyl)-(1→4)-[O-(2,3,4-tri-O-benzyl-α-L-fucopyranosyl)-(1→3)]-6-O-benzoyl-β-D-glucopyranoside (18b)

Compound 17b (50 mg, 9.49×10⁻² mmol) and the sialic acid donor (19, 130 mg, 25×10⁻² mmol) was dissolved in acetonitrile (2.5 ml) and stirred (1 h) in the presence of molecular sieve 4 Å (0.3 g). Silver triflate (237.5 mg, 0.9 mmol) was added and the stirring continued under argon for 2 h. The reaction mixture was cooled (−45° C.), and 80 μl of a freshly prepared solution (990 mg/2.55 ml) of methyl sulfenyl bromide (Dasgupta, F. and Garegg, P. J. *Carbohydr Res* (1988) 177:C13) was introduced into the reaction flask. Reaction was terminated after 2 h by the addition of a solution of triethylamine (0.5 ml) in chloroform (1.5 ml). The reaction mixture was filtered through celite, the filtrate washed with water, lo dried ($MgSO_4$), filtered and evaporated. The residue (0.19 g) was chromatographed from a dry, packed silica gel (80 g) column using 4:1:0.1 (150 ml) and 5:1:0.1 toluene-acetone-methanol as the eluants. Fractions containing the product were evaporated to give the named compound 18b (34.5 mg, 48%), which crystallized from ether, m.p. 194°–195° C., $[\alpha]_D$ −25°, $[\alpha]_{436}$−49° (c 1.0 chloroform). Elem. Anal. Calc. for $C_{80}H_{91}NO_{29}$: %C 62.21; %H 5.99 and N 0.92. Found: %C 62.21; %H 6.23 and %N 0.91.

EXAMPLE 12

O-(5-acetamido-3,5-dideoxy-D-glycero-α-D-galacto-2-nonulopyranosonic acid)-(2→3)-O-(β-D-galactopyranosyl)-(1→4)-[O-(α-L-fucopyranosyl)-(1→3)]-D-glucopyranose (20)

Compound 18 (32 mg) was dissolved in methanol (5 ml) and treated with catalytic NaOMe (6 h). The solution was neutralized by stirring with IR¹²⁰(H⁺) resins at 0°–5° C. The solution was filtered, evaporated, and the residue dissolved in 1:1 10% aqueous MeOH-p-dioxane (5 ml). 0.2M Aqueous KOH (1 ml) was added at 0°–5° C. and hydrolysis of the carboxymethyl group was accomplished in 8 h. The solution was neutralized using IR120(H⁺) resins at 0°–5° C., filtered, and the filtrate evaporated to a syrup. This was dissolved in 10% aqueous MeOH (5 ml) and hydrogenated (1 atm.), in the presence of 5% Pd on carbon (100 mg). Filtration and evaporation of the filtrate afforded a syrup which was eluted through a Biogel P-2 column using water. The appropriate fractions were pooled and lyophilized to afford the named title tetrasaccharide 20 (12 mg), $[\alpha]_D$ −23°, $[\alpha]_{436}$ −46° (c 0.6, $H_2O$).

EXAMPLE 13

Preparation of a Multivalent Ligand, N,6N.6N' Tris (20) Lys-Tyr-Lys

Compound 20, prepared in Example 12, was derivatized to the trisaccharide Lys-Tyr-Lys to obtain the trivalent conjugate derivatized at the two s-amino lysine groups and the α-amino N-terminal of the peptide. To obtain this trivalent compound, 50 μl of 2 mM peptide Lys-Tyr-Lys (100 nmol) in 100 mM sodium carbonate, pH 9, were placed in a small Eppendorf tube containing 5 μl of 200 mM 20 (1 mmol), and the sample was evaporated to dryness in a SpeedVat for about 30 minutes.

After evaporation, 50 μl of 800 mM $NaCNBH_3$ (recrystallized, 40 μmol) in 100 mM sodium carbonate, pH 9, was added and the mixture was incubated for 48 hours at 55° C. The resulting incubated mixture was run on a GPC peptide HPLC sizing column and fractions were collected and assayed for protein content by BCA protein assay. Protein-containing fractions were pooled, lyophilized and submitted for mass spectroscopy.

The results showed the formation of the derivatized peptide as containing 1, 2 or 3 moieties of compound 20.

The trivalent derivative is especially effective in inhibiting the binding of lactose to hepatocytes in an assay conducted as described by Lee, R. et al., *Biochem* (1984) 23:4255.

We claim:

1. A compound of the formula

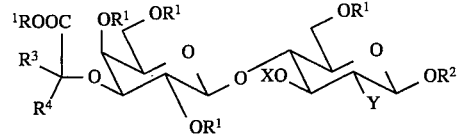

wherein each $R^1$ is independently H or lower alkyl (1–4C);

$R^2$ is H, lower alkyl(1–4C), alkylaryl or at least one additional saccharide residue;

$R^3$ and $R^4$ are each independently H, alkyl(1–6C), aryl or $R^3$ and $R^4$, taken together, form a five- or six-membered ring optionally containing a heteroatom selected from the group consisting of O, S, and $NR^1$;

wherein said five- or six-membered ring may further be substituted by one or more substituents selected from the group consisting of $(CHOR^1)_mH$, wherein m is 1–4, $OR^1$, $OOCR^1$, $NR_2^1$, $NHCOR^1$, and $SR^1$;

Y is H, $OR^1$, $OOCR^1$, $NR_2^1$, $NCOR^1$ or $SR^1$; and

X is —CHR⁵(CHOR¹)₂CHR⁶OR¹ wherein R⁵ and R⁶ result in a five- or six-membered ring optionally containing a heteroatom selected from the group consisting of O, S, and NR¹;

said five- or six-membered ring optionally substituted with one or more substituents selected from the group consisting of R¹, CH₂OR¹, OR¹, OOCR¹, NR¹₂, NHCOR¹, SR¹ and F;

with the proviso that if Y represents NR₂¹, or NCOR¹, then R³ and R⁴, taken together, cannot provide a hexose substituent.

2. The compound of claim 1 wherein all R¹ are H.
3. The compound of claim 1 wherein R² is H.
4. The compound of claim 1 wherein Y is H or OH.
5. The compound of claim 1 wherein X is a 3,4,5-trihydroxypuran- 2-yl, 3,4,5-trihydroxyfuran-2-yl, 3,4,5-trimethoxypyran-2-yl or 3,4,5-trimethoxyfuran- 2-yl.
6. The compound of claim 1 wherein one of R³ and R⁴ is H and the other is H, lower alkyl (1–4C), or phenyl.
7. The compound of claim 6 wherein the lower alkyl is methyl.
8. The compound of claim 6 wherein both R³ and R⁴ are H.
9. The compound of claim 1 wherein R³ and R⁴ taken together are 3,4,5-tri-hydroxypuran-2-yl, 3,4,5-trihydroxyfuran-2-yl, 3,4,5-trimethoxypyran-2-yl or 3,4,5-trimethoxyfuran-2-yl.
10. The compound of claim 1 wherein all R¹ are H, R² is H, both R³ and R⁴ are H, Y is H or OH, and X is a fucosyl residue.
11. A method of synthesizing compounds of claim 1 which method comprises contacting an intermediate compound with an electrophile, wherein the intermediate compound is

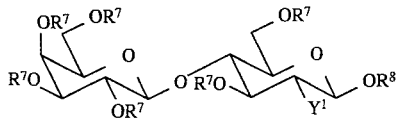

wherein each R⁷ can be substituted by the electrophile and each R⁷ is independently H, lower alkyl (1–4C), or a protecting group; and wherein Y¹ is H, OR⁷, OOCR⁷, NR₂⁷, NCOR⁷ or SR⁷;

wherein the R⁷ that is to be substituted for the electrophile is adjacent to an R⁷ that is an H and each remaining R⁷ is a protecting group;

R⁸ is a protecting group; and wherein the electrophile is substituted for the H of the OH at the position to be substituted.

12. The method of claim 11 wherein the intermediate compound is selected from the group consisting of:

benzyl 6-O-benzoyl-3-O-(2,3,4-tri-O-benzyl-α-L-fucopyranosyl)-4-O-(6-O-benzoyl-β-D-galactopyranosyl)-β-D-glucopyranoside;

benzyl 6-O-benzoyl-3-O-(2,3,4-tri-O-benzyl-[d]α-L-fucopyranosyl)-4-O-(6-O-benzyoyl- 3,4-O-isopropylidene-β-D-galactopyranosyl)-β-D-glucopyranoside;

benzyl 3-O-(2,3,4-tri-O-benzyl-α-L-fucopyranosyl)-4-O-(3,4-O-isopropylidene-β-D-galactopyranosyl)-β-D-glucopyranoside;

benzyl 2,6-di-O-benzoyl-3-O-(2,3,4-tri-O-benzyl-α-L-fucopyranosyl)-4-O-(2,6 -di-O-benzoyl-3,4-O-isopropylidene-β-D-galactopyranosyl)-β-D-glucopyranoside;

benzyl 2,6-di-O-benzoyl-4-O-(2,6-di-O-benzoyl-3,4-O-isopropylidene-β-D-galactopyranosyl)-β-D-glucopyranoside;

2-(Trimethylsilyl) ethyl 3-O-(2,3,4-tri-O-benzyl-α-L-fucopyranosyl)-4-O-(2,6 -di-O-benzoyl-β-D-galactopyranosyl)-2,6-di-O-benzoyl-β-D-glucopyranoside; and benzyl O-(2,3,4-tri-O-benzyl-α-L-fucopyranosyl)-(1–3)-[O-(2,6-di-O-benzoyl-3,4 -O-isopropylidene-β-D-galactopyranosyl)-(1–4)]-2,6-di-O-benzoyl-β-D-glucopyranoside.

13. A conjugate consisting essentially of at least one residue of a compound of the formula 1A

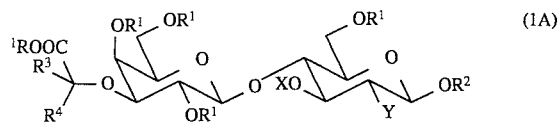

wherein each R¹ is independently H or lower alkyl (1–4C);

R² is H, lower alkyl(1–4C), alkylaryl or at least one additional saccharide residue;

R³ and R⁴ are each independently H, alkyl(1–6C), aryl or R³ and R⁴, taken together, form a five- or six-membered ring optionally containing a heteroatom selected from the group consisting of O, S, and SR¹;

wherein said five- or six-membered ring may further be substituted by one or more substituents selected from the group consisting of (CHOR¹)ₘH, wherein m is 1–4, OR¹, OOCR¹, NR₂¹, NHCOR¹, and SR¹;

Y is H, OR¹, OOCR¹, NR₂¹, NCOR¹ or SR¹; and

X is —CHR⁵(CHOR¹)₂CHR⁶OR¹ wherein R⁵ and R⁶ result in a five- or six-membered ring optionally containing a heteroatom selected from the group consisting of O, S, and NR¹;

said five- or six-membered ring optionally substituted with one or more substituents selected from the group consisting of R¹, CH₂OR¹, OR¹, OOCR¹, NR¹₂, NHCOR¹, SR¹ and F;

with the proviso that if Y represents NR₂¹, or NCOR¹, then R³ and R⁴, taken together, cannot provide a hexose substituent, wherein the compound is coupled to a carrier moiety.

14. The conjugate of claim 13 wherein the carrier moiety is a peptide.
15. The conjugate of claim 14 wherein said peptide is of the formula Lys-Tyr-Lys.
16. The conjugate of claim 13 which contains at least two residues of the compound of Formula 1A.
17. The conjugate of claim 13 which contains at least three residues of the compound of formula 1A.
18. The conjugate of claim 13 wherein the compound of formula 1A is O-(5-acetamido-3,5-dideoxy-D-glycero-α-D-galacto-2-nonulopyranosonic acid)-(2-3)-O-(β-D-galactopyranosyl)-(1-4)-[O-(α-L-fucopyranosyl)-(1–3)]-D-glucopyranose.
19. A pharmaceutical composition comprising said compound of claim 1.
20. A pharmaceutical composition comprising said compound of claim 13.
21. A method of preventing or controlling inflammation in a host, comprising administering to said host an effective amount of the pharmaceutical composition of claim 19.
22. A method of preventing or controlling inflammation in a host, comprising administering to said host an effective amount of the pharmaceutical composition of claim 20.

* * * * *

UNITED STATES PATENT AND TRADEMARK OFFICE
CERTIFICATE OF CORRECTION

PATENT NO. : 5,567,683
DATED : October 22, 1996
INVENTOR(S) : Mina A. NASHED et al.

It is certified that error appears in the above-indentified patent and that said Letters Patent is hereby corrected as shown below:

Col. 5, line 24: delete "lo".

Col. 6, line 29: delete "lo".

Col. 22, line 9: replace "71;2)" with -- 7b) --.

Col. 22, line 35: replace "141;2" with -- 14b --.

Col. 24, line 24: replace "s-amino" with -- $\epsilon$-amino --.

Signed and Sealed this

Fourth Day of March, 1997

BRUCE LEHMAN

*Attest:*

*Attesting Officer*  Commissioner of Patents and Trademarks